United States Patent [19]

Grob

[11] Patent Number: 5,152,739
[45] Date of Patent: Oct. 6, 1992

[54] FIXATION AND MOBILIZATION SPLINT

[76] Inventor: Michael Grob, alte Jonastrasse, CH-8640 Rapperswil, Switzerland

[21] Appl. No.: 658,976

[22] Filed: Feb. 21, 1991

[30] Foreign Application Priority Data

Feb. 23, 1990 [CH] Switzerland .................. 591/90

[51] Int. Cl.⁵ .......................................... A61F 5/01
[52] U.S. Cl. ............................................ 602/5; 602/12
[58] Field of Search ............... 128/87 R, 87 A, 89 R; 602/4, 5, 12, 15, 21, 22

[56] References Cited

U.S. PATENT DOCUMENTS

| 390,176 | 9/1888 | Lee | 128/89 R |
|---|---|---|---|
| 896,674 | 8/1908 | Walker | 128/89 R |
| 1,964,694 | 6/1934 | Longfellow | 128/87 R |
| 3,788,307 | 1/1974 | Kistner | 128/87 R X |
| 3,815,587 | 6/1974 | Guerrant | 128/87 A X |
| 3,815,588 | 6/1974 | Klausner | 128/87 A X |
| 4,190,902 | 3/1980 | Rhee | 128/87 R X |
| 4,558,694 | 12/1985 | Barber | 128/87 A |
| 4,719,906 | 1/1988 | DeProspero | 128/89 R X |
| 4,765,320 | 8/1988 | Lindemann et al. | 128/87 A |
| 4,949,711 | 8/1990 | Gyovai | 128/87 R X |

FOREIGN PATENT DOCUMENTS 3713539 11/1987 Fed. Rep. of Germany .... 128/87 R
590664 1/1976 Switzerland .

OTHER PUBLICATIONS

Rehabilitation of the Hand, 2nd Ed. James M. Hunter, et al, The C.V. Mosby Company, St. Louis, Toronto, 1984.

Primary Examiner—Robert A. Hafer
Assistant Examiner—Sam Rimell
Attorney, Agent, or Firm—Herbert Dubno; Yuri Kateshov

[57] ABSTRACT

The fixation and mobilization splint is fastened to the forearm of the patient and comprises a hand palm support (3) for fixing the palm. This palm support extends from the wrist to the roots of the fingers. It comprises connecting means (4, 8, 14, 15) for securing and exchanging finger supports (11, 12, 13) which are of a definite shape, cross section and curvature for each finger, including the thumb. The angular position between the palm support (3) and that part (2) of the splint (1) that is fastened to the forearm is adjustable.

4 Claims, 4 Drawing Sheets

FIXATION AND MOBILIZATION SPLINT

FIELD OF THE INVENTION

The invention refers to a fixation and mobilization splint.

BACKGROUND OF THE INVENTION

It is known to use a fixation splint for immobilizing the hand joint, the thumb and the other fingers. Such an immobilization is recommended after operations, fractures luxations and overstretches. A mobilization splint is used for recovering the mobility of members, in particular of finger joints, more specifically of thumb joints. A combined fixation and mobilization splint offers the advantage of individually accelerating the healing and adapting process for each member.

In Swiss Patent No. 590 664 there is described a hand and finger orthesis (support for maintaining the hand or the fingers in their usual position with regard to the arm or the palm of the hand). However, that support is only a training device, intended for exercising the various movements of the fingers. These movements are made possible by suspending the fingers on threads only, without any support. However, this suspension prevents fixing a position of the hand or the fingers that promotes the healing process. In addition the threads are suspended from an elastic spring which even promotes the uncontrolled movements and thus further decreases the healing process.

In U.S. Pat. No. 4,719,906 there is described a combined fixation and mobilization splint which comprises a support member for each bone of the finger, including the thumb, the support member being attached to the respective member of the finger by a suitable catch such as e.g. a burr-type catch. The members belonging to a particular finger are connected to each other by means of screws so that the required angle can be adjusted for each support member after having loosened the respective screws by means of a screwdriver. Then the angle of each member with regard to the adjacent one will be set again. The disadvantage of this adjustment resides in the fact that for each joint between adajacent members two screws have to be fastened, a method which has proven to be complicated in practice since for each finger there are three members with a total of six screws which have to be adjusted separately and relatively to each other. In addition the weight of the entire splint which is made of steel becomes uncomfortable for the bearer.

OBJECTS OF THE INVENTION

It is a principal object of the invention to overcome the deficiencies of the known splints and to provide a fixation and mobilization splint of simple design, low weight and comprising definite angular positions for the fingers, also for the thumb, whereby the individual parts of the splint can be assembled practically without the need for tools.

It is another object of the invention to increase the comfort for the patient bearing such a splint.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
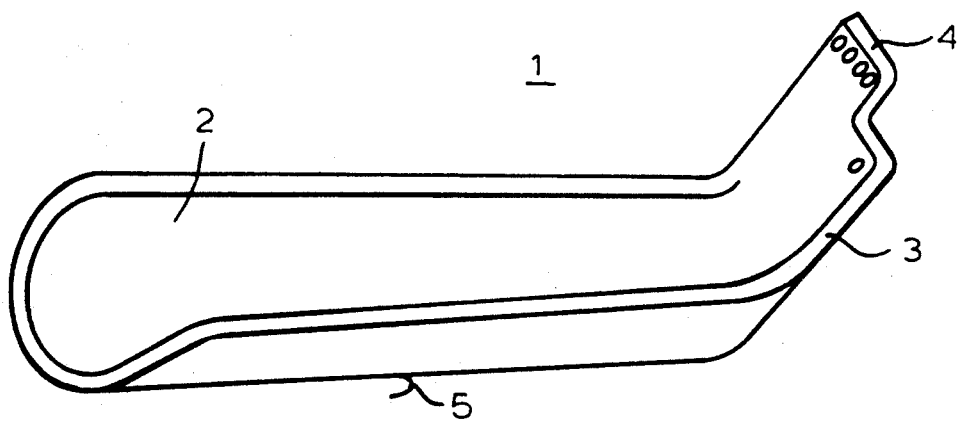
FIG. 1 is a perspective view of a first embodiment according to the present invention with parts integrated into one piece.
Figure 4:
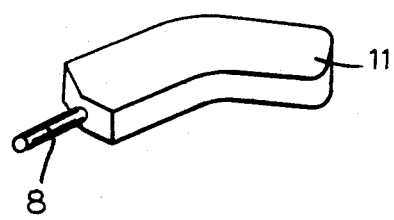
FIG. 4 is a support for the thumb, extending over two of its joints.
Figure 5:
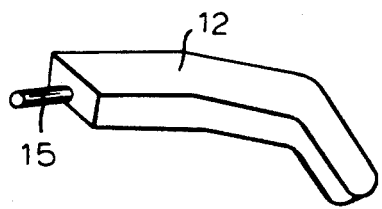
FIG. 5 is a support for another finger, extending over two of its joints.
Figure 6:
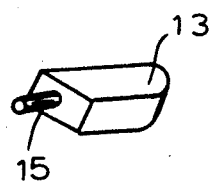
FIG. 6 is a support for a finger extending over its first member.

According to FIG. 1 splint 1 consists of part 2 or trough which is to be attached to the patient's forearm in a known manner, and of hand palm support 3 extending from the wrist to the first finger joints including the one of the thumb. The upper edge of palm support 3 is provided with facilities 4 for attaching supports as shown in FIGS. 4, 5 and 6. The attachments are of the kind illustrated in FIGS. 7, 8 and 9. In palm support 3 facilities 4 are formed as cavities or bores into which supports 11, 12, 13 of FIGS. 4, 5 and 6 can be inserted. For each finger a support having the required curvature the necessary shape and the desired cross section can be provided. It often occurs that only one or another finger needs to be supported. Those fingers that need no therapy receive no supports. In contrast to previous treatments they are not fixed and therefore can be freely moved. For each type of finger, i.e. index, middle, ring or small finger a support 12 having a definite cross section, form and curvature is provided. The supports are either completely prefabricated or prepared of epoxy resin according to the finger that needs therapy. The particular finger which may also be the thumb is attached with known means such as various kinds of ribbon or the like.

Part 2 of splint 1, to be attached to the forearm, and palm support 3 are of one piece and may be made of plastic material. That piece is either prefabricated or is prepared according to the dimensions of the patient's forearm and the position of his palm. FIG. 1 illustrates a splint 1 for the left forearm; a splint for the right forearm can easily be prepared, too.

On the exterior wall of part 2 of splint 1 at least one fixing hook 5 is provided into which one end of a ribbon or thread is inserted, the other end being attached to the thumb or any other finger that needs therapy. With this device the fingers, including the thumb, will be bent during the mobilisation phase. This is achieved by placing the thumb or any other finger on a short support 13 that extends only to the first finger joint or to bring it into a claw position by means of the ribbon or the thread, without the use of a support. This procedure is repeated so often as prescribed by the therapy plan. There is also the possibility of altering the curvature of the fingers by simply substituting supports 11, 12, 13 by those having a different curvature, the thumb or any other finger being attached to the respective support in known manner.

Figure 2:
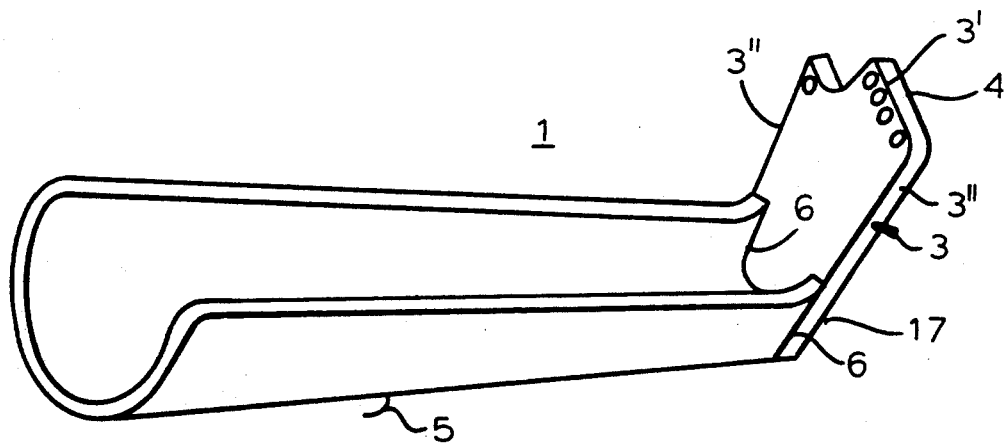
FIG. 2 is a perspective view of a second embodiment according to the invention with parts assembled.

FIG. 2 illustrates a splint 2 whose parts 2 and 3 are assembled. The advantage of this embodiment resides in the fact that different palm supports 3 can be attached to forearm part 2. e.g. a support 3 for big or small palms and for left and right hands. The correct angle to be assumed by palm support with regard to the forearm is assured by guide means 6. These guide means 6 is according to FIG. 2. represented by the surfaces of forearm part 2 onto which palm support 3 comes to rest. Guide means 6 may have a required angle of inclination. Other guide means may also be provided on palm support 3 in the form of wedges 9 having the required angle. Palm support 3 is connected to part 2 either solidly or releasably. Glue or screw connection 17 is represented only schematically in FIG. 2. The kind of connection depends upon the ideas of the therapist with regard to the process of the therapy or the re-use of parts 2 and 3. If during the course of the therapy the angular position of the hand and/or the thumb or the other fingers must be altered, another forearm part 2 or another palm support 3, both having different guide means 6 respectively 9, and/or supports 11, 12, 13 formed with two members 11'' and 11''' and having different shapes, cross sections or cuvatures may be used. These supports are illustrated in FIGS. 4, 5 and 6, and they can releasably be attached to the upper edge 4' bridging lateral edges 4'' of palm support 3 by means of one of the connecting facilities shown in FIGS. 7, 8 and 9. To this effect cavities are used. For each support a pin 8, 15 or a projection 14 is used and will be inserted into the respective bore or groove. There is also the possibility of using two pins for one support, said pins being introduced into corresponding bores. In this case pins 8, 15 prefeably are arranged on the upper edge of palm support 3 whilst the finger supports are equipped with bores for receiving the pins. These connections are releasable, too.

Figure 3:
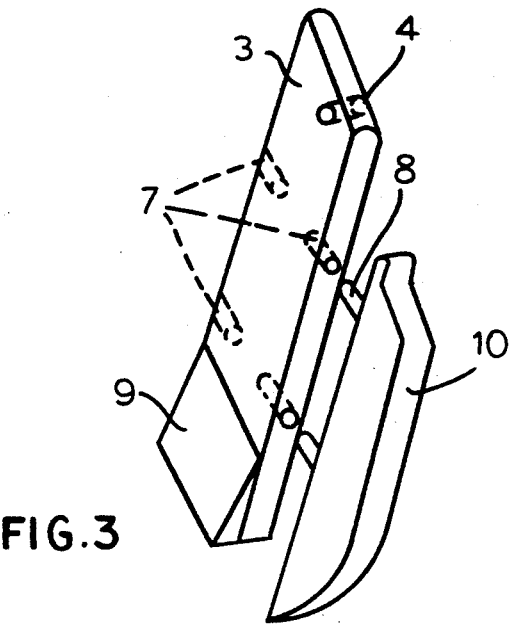
FIG. 3 is a view of a part of this second embodiment.
Figure 7:
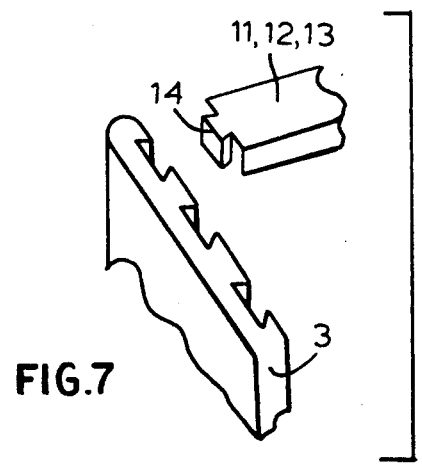
FIGS. 7–13 are perspective, exploded and sectional views representing various means of connection between supports and hand palm support as well as between hand palm support and thumb support.

FIG. 3 illustrates a palm support 3 onto which a thumb support 10 is attached on either one or the other side. This renders it possible to use the same palm support for either the left or the right hand, whereby the same thumb support 10 can be used for either hand, too. Palm support 3 and thumb support 10 may be manufactured from wood or plastics. FIG. 3 further illustrates connecting means consisting of two pins 8 on the lateral side of thumb support 10, to be inserted into corresponding bores 7 in the lateral side of palm support 3. The connection means is of the kind shown in FIG. 8. However, connecting means may also be as illustrated in FIGS. 7 and 9. During the course of therapy, palm support 3 and thumb support 10 may be exchanged and re-used again at a later time.

FIG. 4 illustrates a thumb support 11, made of plastics or wood and consisting of one piece and having a particular form, curvature and cross section. Since the thumb must be supported in different curvatures during the therapy, different thumb supports 11 will be used; one support subsequently being exchanged against another one. The correcting means shown in FIG. 4 consists of a pin 8 which is inserted into bore 4 on the upper edge of palm support 3 (FIG. 3). For clarifying FIG. 3, bore 4 is represented only schematically.

Another support, numbered 12, for a finger is illustrated in FIG. 5 and also is made of wood or plastics. This support, too, has a particular cross section, a particular form and curvature and extends over the entire length of a finger. It is conceived for all fingers except the thumb. Here, too, the various curvatures that a particular finger must assume during its therapy are achieved by using supports 12 of different curvatures. The supports can be exchanged. They are releasably connected to the upper edge of palm support 3 by means of one of the connections shown in FIGS. 7, 8 or 9. The support according to FIG. 5 has a connecting member as represented in FIG. 9, the member being a metal sleeve 15 which is to be inserted into bore 4 and secured by a screw 16.

FIG. 6 represents a support 13 that extends only to the first member of a finger and is manufactured from wood or plastics. This support has a definite form and a definite cross section, according to the finger to be supported, be it the index, middle, ring or the small finger. The releasable connection to the upper edge of palm support 3 may be one of those illustrated in FIGS. 7, 8 and 9. The exchangeability of support 13 is assured in any case.

FIG. 7 illustrates a dove-tailed connecting facility 14 between palm support 3 and finger supports 11, 12, 13. These supports will be inserted into the grooves but can be removed from them at any time in order to assure their exchangeability. Each groove in palm support 3 is as wide as the corresponding dove-tail of the finger support.

Figure 8:
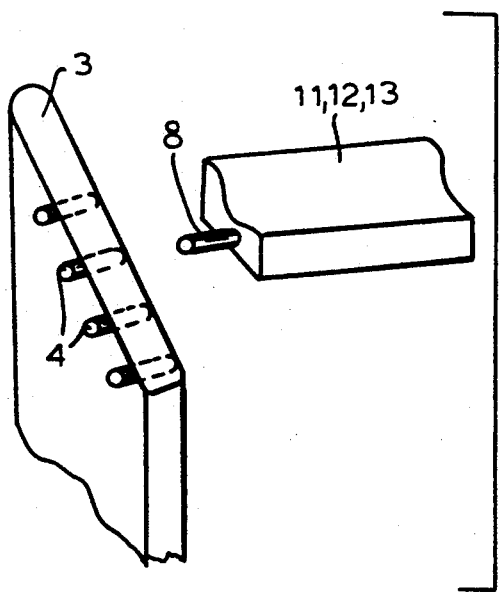
Figure 9:
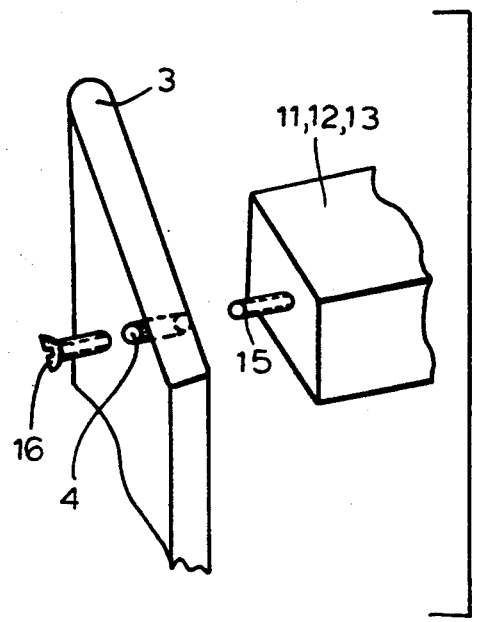

FIG. 8 shows a connecting facility which comprises a pin 8 attached to support 11, 12, or 13, and a bore 4 on the upper edge of palm support 3 for receiving pin 8. The finger support can be removed at any time from palm support 3 and replaced by another support if required. In this figure pin 8 and bore 4 are illustrated as having circular cross sections, for reasons of simplicity. However, their cross sections may as well be polygonal or elliptic. The non-circular cross-sections are recommended if a stable position of supports 11, 12 and 13 relatively to palm support 3 is of particular importance.

The connection represented in FIG. 9 consists of a metal sleeve 15 having an interior thread and secured in support 11, 12 respectively 13. Sleeve 15 is inserted into bore 4 of palm support 3 and secured at its other end by a screw 16 which is screwed so far into the interior thread of sleeve 15 until its head is fully sunk. Also with this connecting facility the exchangeability is assured in every respect.

Figure 10:
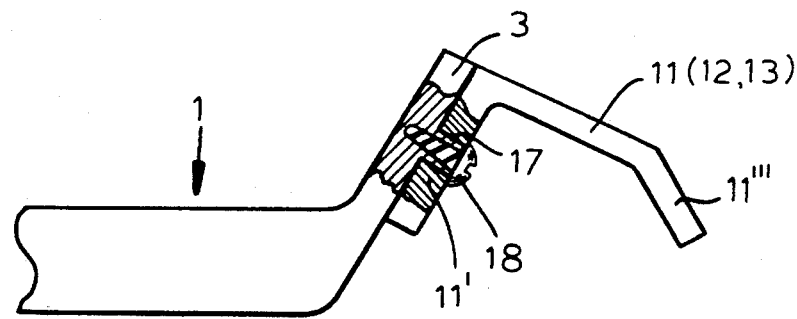

FIGS. 10 to 13 disclose further means of connecting finger supports 11, 12 and 13 to palm support 3. In FIG. 10 support 11 which is shown vicariously also for supports 12 and 13 is supplemented by an arm 11' that extends at a generally right angle from it. The exact angle of this arm relative to the support depends upon the angular position the latter assumes with regard to palm support 3, i.e. that position must be the same as on the embodiments according to FIGS. 7 to 9 whereas arm 11' extends parallel to palm support 3. In arm 11' there is a bore 17. A wood screw 18 is inserted into it so that it protrudes from that bore with its one end and is screwed into palm support 3 with the aid of a screw driver. The advantage of this kind of securing the finger support to the palm support remains in the fact that one can adapt the position of support 11 relatively to palm support 3 exactly to the hand of the patient. First support 11 is brought into the proper position according to the patient's hand. Then a drill is passed through bore 17 for drilling a cavity into palm support 3. Now finger support 11 and palm support 3 can be removed from the patient, and support 11, by means of its arm 11', can definitely be secured to palm support by inserting screw 18.

Figure 11:
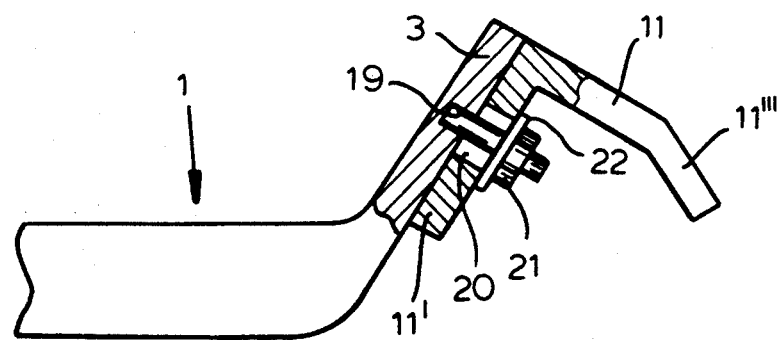

This method of securing support 11 by means of a screw can be adapted even better to the patient's needs with the embodiment according to FIG. 11. Wood screw 18 is substituted by a threaded pin 19 inserted solidly into palm support 3. Bore 17 is widened to an oblong hole 20, and arm 11' is then placed onto pin 19 so that the latter extends through the oblong hole 19. Thanks to this hole, the definite position of support 11 with regard to palm support 3 can be adjusted directly on the patient and afterwards secured by screwing a nut 21 with a washer 22 onto threaded pin 19. In contrast to the previous embodiment, the present one can be used over and over again, i.e. individually adjustable for different patients.

Figure 12:
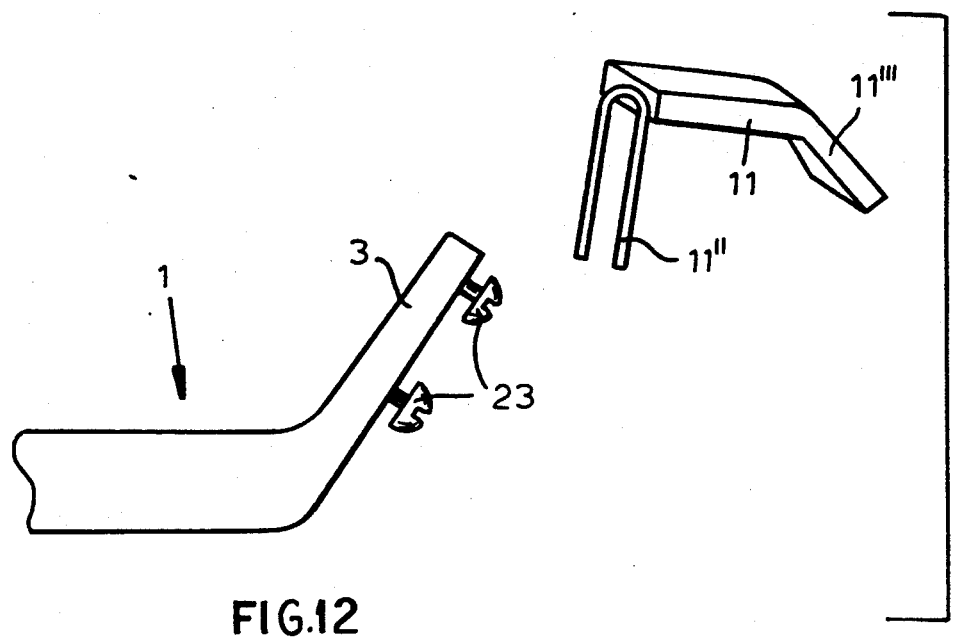

The same holds good for the embodiment according to FIG. 12. Arm 11', however, is replaced by a U-shaped clasp 11' which is rigidly secured to that face of support 11 onto which, on the embodiments according to FIGS. 4 to 6, pin 8 or sleeve 15 is attached. Clasp 11' may also be substituted by an elongated plate having a U-shaped slot that is open on the free end of the plate. Two cap screws 23 inserted into palm support 3 one behind the other and surrounded by the clasp or plate, are tightened and thus solidly hold the clasp or plate. Here, too, the exact adjustment can be carried out on the patient and immediately become fixed so that any subsequent inadvertent dislocation is avoided. In order to clarify FIG. 12, support 11 is illustrated separate from splint 1 and additionally is shown in a position that is at a slight angle to palm support 3.

Figure 13:
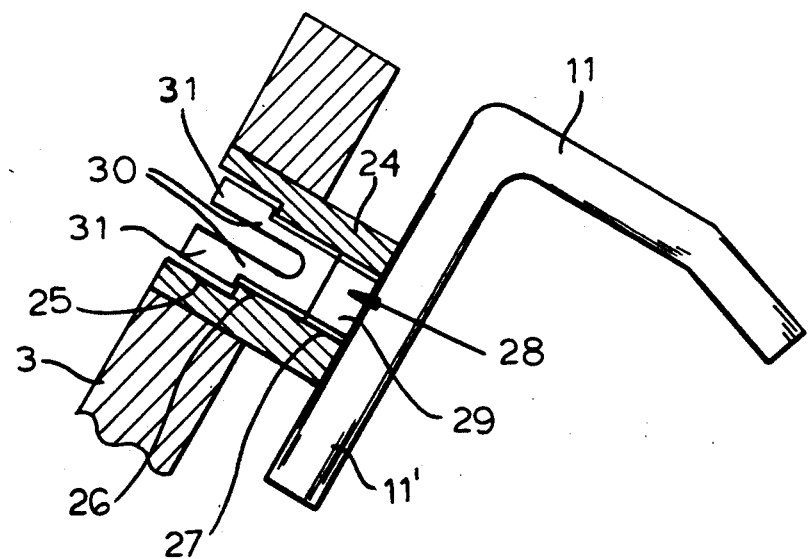

Finally FIG. 13 shows yet another kind of connecting support 11 to palm support 3. Support 11 again has an arm 11'. A nearly cubical body 24 is located within palm support 3, the body having a through bore that consists of three sections 25, 26 and 27. Section 25 has a circular cross section as well as section 26 which, however, is of a smaller diameter. Section 27 is square in its cross section. Arm 11' bears a projection 28 which in turn possesses a section 29 adapted to fit in to section 26, i.e. of square cross section, too, as well as two tongues 30. Their exterior surface is circular in cross section and each tongue is equipped with an enlargement 31 at its tip which fits into section 25. Since the tongues are distant from each other and furthermore elastically deformable, they can easily be pushed through the narrow sections 26, 27. In section 27 they diverge again, and thus projection 28 is solidly anchored at the junction of sections 25, 26. Since in this position rectangular section 29 is located within equally recangular section 27, projection 28 and with it finger support 11 are also secured against rotational movements about the longitudinal axis of projection 28. In order to remove support 11, a tensile load perpendicularly to palm support 3 is applied on it. The tongues therefore approach each other again because enlargements 31 are rounded off at one end, and can easily be pulled out of narrow sections 26, 27.

In view of the many possibilities of connecting palm support 3 to part 2 of splint 1 and finger supports 11, 12, 13 to palm support there is provided a universal fixation and mobilisation splint wich fulfils the many needs occuring during the course of a therapy by means of simple parts of low manufacturing costs.

I claim:
1. A stabilizing splint for a hand permitting selective finger mobility, said splint comprising:
 a trough supporting a forearm and for preventing arbitrary lateral movements of the forearm;
 a palm support rigid with said trough and supporting a wrist of the hand distal to said forearm, said palm support extending outwardly at an obtuse angle from said trough and being formed with:
 a front edge spaced from said trough,
 a pair of lateral edges extending between said trough and said front edge, and
 means forming at least four recesses in said palm support close to said outer edge, each of said recesses being a hole having a predetermined shape cross section; means forming at least four finger supports each adapted to support separately an individual finger of the hand, each of said finger supports including:
 a respective proximal longitudinal member, and
 a respective distal longitudinal member extending downwardly at an angle from said proximal member, said members forming a respective one-piece rigid finger support having a shape conforming to a respective finger resting in a protective position; and
 fastening means for mounting the finger supports on said palm support, said fastening means including:
 at least one threaded metal pin on the respective proximal member selectively connecting the respective finger support with a respective one of said recesses, and having a cross section corresponding to the shape of said hole, and
 countersunk screws, said pin being mounted in the respective hole and secured therein by the respective countersunk screw, so that at least one finger to be stabilized rests in the protected position while other fingers are able to move.

2. A stabilizing splint for a hand permitting selective finger mobility, said splint comprising:
 a trough supporting a forearm and for preventing arbitrary lateral movements of the forearm;
 a palm support rigid with said trough and supporting a wrist of the hand distal to said forearm, said palm support extending outwardly at an obtuse angle from said trough and being formed with:
 a front edge spaced from said trough,
 a pair of lateral edges extending between said trough and said front edge, and
 means forming at least four recesses in said palm support close to said outer edge, each of said recesses being formed as a dove-tail cavity;
 means forming at least four finger supports each adapted to support separately an individual finger of the hand, each of said finger supports including:
 a respective proximal longitudinal member, and
 a respective distal longitudinal member extending downwardly at an angle from said proximal member, said members forming a respective one-piece rigid finger support having a shape conforming to a respective finger resting in a protective position; and
 fastening means for mounting the finger supports on said palm support, said fastening means including at least one protrusion on the respective proximal member selectively connecting the respective finger support with a respective one of said recesses, said protrusion having a corresponding dove-tail shape fitting in the respective one of said recesses, so that at least one finger to be stabilized rests in the protected position while other fingers are able to move.

3. A stabilizing splint for a hand permitting selective finger mobility, said splint comprising:

a trough supporting a forearm and for preventing arbitrary lateral movements of the forearm;

a palm support rigid with said trough and supporting a wrist of the hand distal to said forearm, said palm support extending outwardly at an obtuse angle from said trough and being formed with:

a front edge spaced from said trough, a pair of lateral edges extending between said trough and said front edge, and means forming at least four recesses in said palm support close to said outer edge, each of said recesses being provided with a respective screwthread;

means forming at least four finger supports each adapted to support separately an individual finger of the hand, each of said finger supports including:

a respective proximal longitudinal member, and a respective distal longitudinal member extending downwardly at an angle from said proximal member, said members forming a respective one-piece rigid finger support having a shape conforming to a respective finger resting in a protective position; and fastening means for mounting the finger supports on said palm support, said fastening means including:

at least one protrusion on the respective proximal member selectively connecting the respective finger support with a respective one of said recesses, said protrusion being a U-shaped clasp provided with a pair of legs defining a slot therebetween, and at least one screw having a head and received by a respective recess, said protrusion receiving the head of the screw pressing against the respective legs upon fastening, so that at leasst one finger to be stabilized rests in the protected position while other fingers are able to move.

4. A stabilizing splint for a hand permitting selective finger mobility, said splint comprising:

a trough supporting a forearm and for preventing arbitrary lateral movements of the forearm;

a palm support rigid with said trough and supporting a wrist of the hand distal to said forearm, said palm support extending outwardly at an obtuse angle from said trough and being formed with:

a front edge spaced from said trough, a pair of lateral edges extending between said trough and said front edge, and means forming at least four recesses in said palm support close to said outer edge, each of said recesses being formed with a respective inner member having an outer surface in contact with an interior surface of the respective recess and a through bore provided with a respective inner surface including:

a first inner section having a circular cross-section with a first diameter, a second circular inner section located outwardly from and next to the first section and provided with a second diameter less than said first one, and a third section next to said second one and having a generally square cross section;

means forming at least four finger supports each adapted to support separately an individual finger of the hand and including:

a respective proximal longitudinal member, and a respective distal longitudinal member extending downwardly at an angle from said proximal member, said members forming a respective one-piece rigid finger support having a shape conforming to a respective finger resting in a protective position, each of said finger supports being formed with an arm extending downwardly at a generally right angle from the respective proximal member; and fastening means for mounting the finger supports on said palm support, said fastening means including at least one protrusion on the respective proximal member selectively connecting the respective finger support with a respective one of said recesses, said protrusion being deformable upon loading and being formed with respective three sections formed with outer surfaces abutted by the corresponding first, second and third inner sections of said inner surface of the respective recess, the section of the protrusion member abutted by the first section of the respective inner member including two tongues spaced apart and pressing against the inner surface of said first inner section providing a reliable mounting of the finger support on said palm support, so that at least one finger to be stabilized rests in the protected position while other fingers are able to move.

* * * * *